(12) United States Patent
Harttig

(10) Patent No.: US 7,922,694 B2
(45) Date of Patent: Apr. 12, 2011

(54) DRIVE DEVICE FOR A PISTON IN A CONTAINER CONTAINING A LIQUID PRODUCT

(75) Inventor: Herbert Harttig, Neustadt (DE)

(73) Assignee: Roche Diagnostics GmbH (DE)

( * ) Notice: Subject to any disclaimer, the term of this patent is extended or adjusted under 35 U.S.C. 154(b) by 1240 days.

(21) Appl. No.: 11/521,239

(22) Filed: Sep. 14, 2006

(65) Prior Publication Data

US 2007/0093751 A1    Apr. 26, 2007

(30) Foreign Application Priority Data

Sep. 30, 2005  (EP) .................................. 05021508

(51) Int. Cl.
*A61M 1/00* (2006.01)
*A61M 5/315* (2006.01)
(52) U.S. Cl. ........................................ 604/151; 604/218
(58) Field of Classification Search ............... 604/890.1, 604/891.1, 131, 151, 218
See application file for complete search history.

(56) References Cited

U.S. PATENT DOCUMENTS

| 5,222,362 A | 6/1993 | Maus et al. |
| 6,723,072 B2 | 4/2004 | Flaherty et al. |
| 2003/0060767 A1 | 3/2003 | Peter et al. |

FOREIGN PATENT DOCUMENTS

WO   WO 03/103763   * 12/2003

OTHER PUBLICATIONS

Carlen, Mastrangelo: "Simple, high actuation power, thermally activated paraffin microactuator", presented at the Transducers 1999 Conference, Sendai, Japan, Jun. 7-10, 1999.*
"Paraffin Wax: Tensile Strength and Density at Various Temperatures," W.F. Seyer and Kuramitsu Inouye, Industrial and Engineering Chemistry, vol. 27, No. 5, May 1935, pp. 367-370.*

* cited by examiner

*Primary Examiner* — Nicholas D Lucchesi
*Assistant Examiner* — Andrew M Gilbert
(74) *Attorney, Agent, or Firm* — Barnes & Thornburg LLP

(57) ABSTRACT

A drive device for a piston in a container containing a liquid comprises a first segment positioned between a second segment and an outlet of the container. The first and second segments each have a first shape in which the respective segment is clamped between lateral walls of the container and a second shape in which the respective segment is released from the lateral walls. A first actuator is configured to vary the first segment between its first and second shapes, and the first segment is in its first shape when the first actuator is inactive. A second actuator is configured to vary the second segment between its first and second shapes, and the second segment is in its second shape when the second actuator is inactive. A connecting segment connects the first segment to the second segment and has an actively variable connecting length.

18 Claims, 3 Drawing Sheets

DRIVE DEVICE FOR A PISTON IN A CONTAINER CONTAINING A LIQUID PRODUCT

CROSS-REFERENCE TO RELATED APPLICATIONS

This application is a U.S. counterpart application of, and claims priority to, European Application Serial No. EP05021508.6 filed Sep. 30, 2005.

FIELD OF THE INVENTION

The invention relates to a drive device which drives a piston in a container, wherein the container contains a liquid product which is driven out of the container through an outlet by the piston. Such drive devices may be used, in particular, for dosing an injectable liquid product (insulin, for example) in an infusion system.

BACKGROUND OF THE INVENTION

The continuous infusion of medicines, or discontinuous, controlled infusion such as that required, for example, when administering insulin, is generally carried out by means of so-called syringe pumps. Here the piston of a syringe is pushed forwards continuously or discontinuously by a suitable plunger and a medicine is administered to the patient via a hose connection and an injection cannula.

In patients with diabetes, the use of a pump for the application of insulin greatly facilitates the daily management of the disease. Here it is desirable that such an insulin pump be small in size and light weight. Precision, reliability and simple operation are generally assumed.

WO 01/72358 A1 discloses a drive device for a piston in a container containing an injectable product. This drive device contains a plurality of displacement stages and a drive for advancing the displacement stages, which drive acts on the displacement stages by means of spindle drives.

U.S. Pat. No. 6,723,072 B2 relates to a device for administering a liquid medicine with a piston arrangement which contains a shape memory element which is arranged between two segments and can alter its length. By alternately lengthening and shortening the shape memory element the piston arrangement is caused to perform a longitudinal movement since the two segments can essentially only be displaced in one direction.

SUMMARY OF THE INVENTION

The present invention may comprise one or more of the following features and combinations thereof.

A drive device is provided for a piston in a container containing a liquid product, wherein the container has limiting lateral walls which extend in the longitudinal direction to an outlet for the liquid product. The drive device contains a first segment facing the outlet, with an actively variable shape, which segment is clamped in a first shape between the lateral walls of the container and is largely released from the lateral walls in a second shape. Furthermore, the drive device contains a second segment facing away from the outlet, with an actively variable shape, which segment is clamped in a first shape between the lateral walls of the container and is largely released from the lateral walls in a second shape. A connecting segment is arranged between the first and second segment and connects the first and second segments together. The connecting segment has an actively variable connecting length.

The drive device is arranged in the container in which the liquid product is also present, wherein the piston separates the drive device from the liquid product.

The outlet of the container may be located, for example, in the lateral walls of the container or may be arranged at its end perpendicular to the lateral walls.

The first and second segment of the drive device according to the invention have an actively variable shape. In this connection actively variable means that the change in shape is brought about and controlled specifically by external interventions (e.g. by applying an electrical current, supply or dissipation of heat, etc.). In this case the change of shape is reversible and is, if necessary, combined with a change in volume of the segment concerned.

When the respective first or second segment assumes its first shape it is clamped between the lateral walls of the container. In this case there is illustratively a frictional force connection between the segment and the lateral walls, which connection prevents the segment from being displaced in the container.

When the respective first or second segment assumes its second shape it is largely released from the lateral walls so that it is displaceable in the container (particularly in the longitudinal direction towards the outlet of the container).

Both segments are connected to each other by the connecting element which has an actively variable length. The distance between the two segments is therefore varied by varying the length of the connecting element. The length variation is reversible. In this connection actively variable means that the length variation is brought about and controlled specifically by external interventions (for example by applying an electrical current, heat supply or dissipation, etc.). The length variation may, in particular, be combined with a variation in volume of the connecting element.

With the drive device according to the invention the liquid product is dosed from the container when the drive device displaces the piston in the container towards the outlet, thus forcing the liquid product out through the outlet. To achieve such displacement of the piston both segments and the connecting segment perform the following sequence of movements:

clamping the second segment between the lateral walls by active variation in the shape of the second segment, release of the first segment from the lateral walls by active variation in the shape of the first segment, increasing the length of the connecting segment, wherein the first segment is displaced in the direction of the outlet, clamping the first segment between the lateral walls by active variation in the shape of the first segment, release of the second segment from the lateral walls by active variation in the shape of the second segment, and reducing the length of the connecting segment, wherein the second segment is displaced in the direction of the outlet, wherein the first and second segments comprise first and second actuators for active variation of the shape of the first and second segments respectively, which actuators are paraffin actuators.

The first segment is in direct contact with the piston and pushes it onto the outlet of the container during its movement. The first segment is illustratively rigidly connected to the piston or designed integrally with the piston. This prevents the piston, for example, from moving without the drive device and also prevents liquid product from accidentally escaping (for example due to a vacuum at the container outlet). The rigid (if necessary releasable) connection between the piston and the fist segment of the drive device may, for example, be made by means of a snap connection, a magnetic coupling or with a suitable actuator.

The first and second segments comprise first and second actuators, respectively, for active variation of the shape of the first and second segments respectively. Furthermore, the connecting element itself is also designed as an actuator or it comprises an actuator for actively obtaining the length variation of the connecting element. Here the actuators can be activated by current or heat, in particular, so that when each actuator is activated the shape of the associated segment is varied and the length of the connecting element is varied. When the actuator is activated there is an increase in volume, for example, which is brought about by thermal expansion or a phase shift, for example, as a result of which a force is exerted at least on sections of the segment, which gives rise to clamping or releasing of the segment from the lateral walls of the container. The entire segment itself may be an actuator in one embodiment of this invention.

The actuators are paraffin actuators, wherein the drive device comprises heating elements for heating the paraffin actuators. Such actuators are described, for example, in Carlen, Mastrangelo: "Simple, high actuation power, thermally activated paraffin microactuator", presented at the Transducers 1999 Conference, Sendai, Japan, 7 to 10 Jun. 1999. Paraffin actuators have different properties than shape memory alloys. For example, the maximum length variation of the shape memory alloys is about 5%. Larger components or lever systems are therefore required to achieve desired actuation lengths. These lengths must be no less than a minimum value since the elastic deformation of the piston must be exceeded before a relative movement takes place between the piston and container wall. With a volume expansion of >15% paraffin actuators allow relatively higher linear expansion and hence a smaller design. Moreover, because of the working temperature within the range of 60° C., the thermal losses with parafin actuator, are comparatively smaller. The temperatures for phase shift in shape memory alloys are in the neighborhood of 100° C., which gives rise to a greater heat loss and hence lower efficiency of the drive.

According to an illustrative embodiment of this disclosure, the first segment is designed so that when a first actuator is not activated it is present in the second shape, and the second segment is designed so that when a second actuator is not activated it is present in the first shape. In the case of an inactive first actuator, the first segment is therefore released from the lateral walls of the container, whilst the second segment is clamped between the lateral walls of the container in the case of an inactive second actuator. Therefore, when all the actuators are deactivated and no energy is consumed, the drive is nevertheless clamped between the lateral walls of the container and cannot be displaced without specific activation of the actuators.

According to one embodiment of this disclosure the container is an ampoule of a circular cross section and the first and second segments comprise clamping rings which can be clamped between an inner wall of the ampoule or released from it by means of in each case one actuator. Here the clamping rings illustratively each have a ring diameter which can be varied by activating the actuators. The clamping rings themselves may be actuators, for example bimetallic rings which open and contract at the time of activation, depending on the structure. In this case no additional actuators are required for the segments.

According to an illustrative embodiment of this disclosure the first segment is designed as an open ring with two tongues projecting into the ring, wherein an actuator, whose thickness is actively variable, is arranged between the two tongues. Furthermore, the second segment may be designed as an open ring with two tongues projecting into the ring, wherein one of the tongues and a thrust bearing arranged adjacent to the other tongue are connected to a baseplate and an actuator, whose thickness is actively variable, is arranged between the other tongue and the thrust bearing. Securing a tongue and the thrust bearing to the baseplate ensures that there is a permanent spatial relationship between one of the tongues and the thrust bearing.

To control the position of the drive device or the piston in the container, a measuring system may be used on the basis of laser triangulation, for example. It is therefore possible to determine the exact position of the piston in the container by means of suitable electronic processors. The dosed quantity of liquid product may be derived from this and the step width of the next cycle can be adapted to the desired dose.

This disclosure further relates to the use of the drive device for dosing a liquid product in an infusion system. The drive device may, in particular, be used in a pump for the application of insulin from an ampoule. However, its use is not limited to this but other active substance solutions may therefore be applied in human or veterinary medicine, particularly when a small, light, portable pump is required. The drive device is also suitable for transporting perfusion fluid from continuous microdialysis. In technical systems a pump with a drive device according to this disclosure can be used to dose small quantities of lubricants or reagents, for example, in the most varied applications.

This disclosure also relates to a method for dosing a liquid product by displacing a piston in a container containing the liquid product by means of a drive device, wherein the container has limiting lateral walls which extend in the longitudinal direction towards an outlet for the liquid product and the drive device comprises a first segment facing the outlet, a second segment facing away from the outlet and a connecting segment arranged between the two segments and connecting them together, with the following method steps:
  clamping the second segment between the lateral walls by active variation in the shape of the second segment,
  release of the first segment from the lateral walls by active variation in the shape of the first segment,
  increasing the length of the connecting segment, wherein the first segment is displaced in the direction of the outlet,
  clamping the first segment between the lateral walls by active variation in the shape of the first segment,
  release of the second segment from the lateral walls by active variation in the shape of the second segment, and
  reducing the length of the connecting segment, wherein the second segment is displaced in the direction of the outlet.

Here the method steps are carried out cyclically in this sequence, the first method step being carried out after the last one. The position of rest of the drive device is achieved, for example, after the second method step is carried out, when the second segment has been clamped, the first segment has been released and the connecting segment has a short length. Due to the sequence of movements mentioned in the method steps, the drive device moves "caterpillar fashion" towards the outlet of the container and pushes the piston forwards and hence pushes the liquid product out of the container through the outlet.

DESCRIPTION OF THE ILLUSTRATIVE EMBODIMENTS

Figure 1:
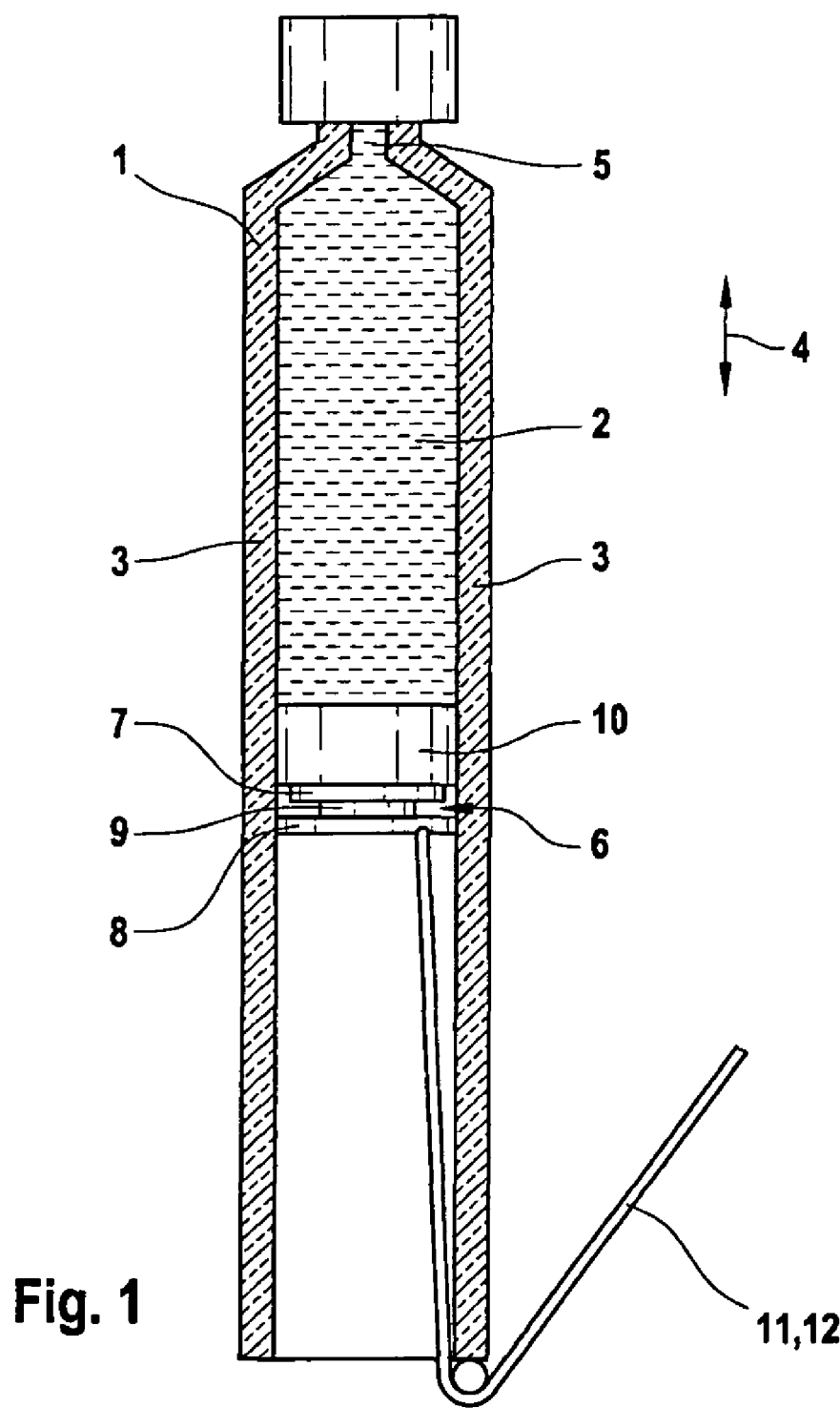
FIG. 1 shows an ampoule with a piston in which a drive device according to this disclosure is inserted.

The container 1 is an ampoule which contains a liquid product 2 (insulin, for example). The container 1 has limiting lateral walls 3 which extend in longitudinal direction 4 to an outlet 5 for liquid product 2. A displaceable piston 10 is arranged in the container 1. The drive device 6 according to this disclosure has a first segment 7, a second segment 8 and a connecting segment 9. The connecting segment 9 has an actively variable length (connecting length), this length determining the distance between the two segments 7, 8. The piston 10 separates the drive device 6 from the liquid product 2 and is rigidly connected to the first segment 7 of the drive device 6 so that although the segment 7 can actively vary its shape, it lies directly in contact with the piston 10 at all times. In the position of rest the drive device 6 (at least one segment) is clamped in the container 1 between the lateral walls, thereby retaining the piston 10 in its position. The signal and energy supply 11 to the drive device 6 takes place via the cable 12.

Figure 2A:
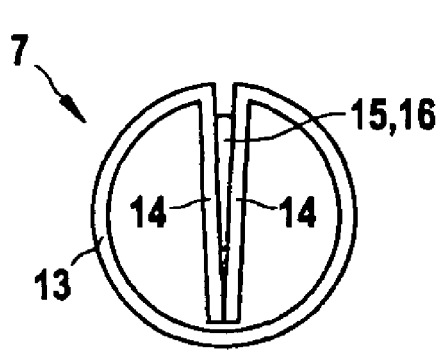
FIGS. 2a and 2b show an embodiment of a first segment of the drive device.
Figure 2B:
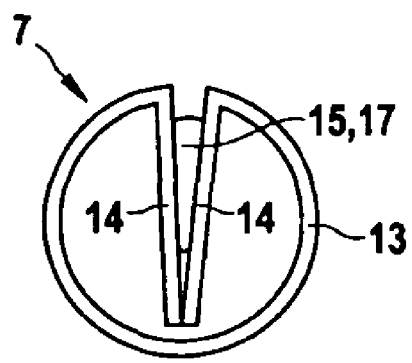

FIGS. 2a and 2b show an embodiment of the first segment 7 of the drive device 6.

The first segment 7 is designed as an open ring 13 with two tongues 14 projecting into the ring 13, wherein a first actuator 15 is arranged between the two tongues 14, this actuator being a paraffin actuator, for example. The thickness of the actuator 15 is actively variable by heating and cooling the actuator 15, for example.

The first segment 7 shown in FIG. 2a shows the actuator 15 when it is deactivated (16). The segment 7 is located in its position of rest with a first smaller ring diameter. With this smaller ring diameter the segment 7 would be released from the lateral walls of a surrounding container and would be displaceable in it. The first segment 7 of the drive device 6 has an actively variable shape. Such a shape variation is achieved by activating the actuator 15.

The first segment 7 shown in FIG. 2b shows the actuator 15 when activated (17). The segment 7 is located in a straddled position with a second larger ring diameter, since the activated actuator 17 pushes the tongues 14 apart because of its greater thickness. With this larger ring diameter the segment 7 would be clamped between the lateral walls of a surrounding container and would be largely non-displaceable in it.

In order to regain the position of rest (FIG. 2a) of the first segment 7, the actuator 15 is deactivated again.

Figure 3A:
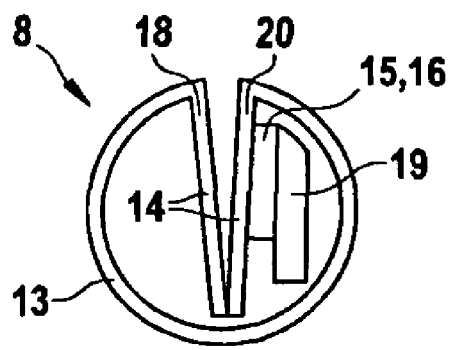
FIGS. 3a and 3b show an embodiment of a second segment of the drive device.
Figure 3B:
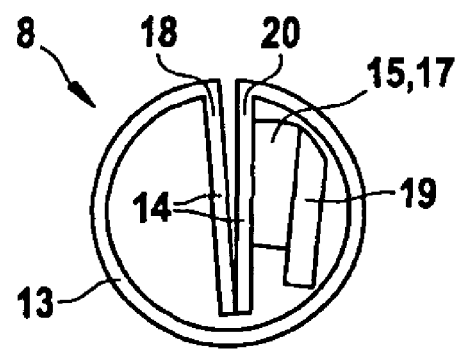

FIGS. 3a and 3b show an embodiment of the second segment 8 of the drive device 6.

The second segment 8 is designed as an open ring 13 with two tongues 14 projecting into the ring 13. The left tongue 18 and a thrust bearing 19, which is arranged adjacent to the right tongue 20, are connected to a baseplate (not shown—lying in the image plane). A second actuator 15, whose thickness is actively variable (for example by heating or cooling) is arranged between the right tongue 20 and the thrust bearing 19.

The second segment 8 shown in FIG. 3a shows the actuator 15 when it is deactivated (16). The segment 8 is located in its position of rest with a first larger ring diameter. With the larger ring diameter the segment 8 would be clamped between the lateral walls of a surrounding container and would be largely non-displaceable in it. The second segment 8 of the drive device 6 has an actively variable shape. Such shape variation is achieved by activating the actuator 15.

The second segment 8 shown in FIG. 3b shows the actuator 15 when it is activated (17). The segment 8 is located in a compressed position with a second smaller ring diameter, since the actuator 17, which is supported on the thrust bearing 19, pushes the right tongue 20 towards the left tongue 18 by its expansion. With this smaller ring diameter segment 8 would be released from the lateral walls of a surrounding container and would be displaceable in it.

In order to regain the position of rest (FIG. 3a) of the second segment 8, the actuator 15 is again deactivated.

FIGS. 4a to 4g show a sequence of movements of a drive device 6.

Figure 4A:
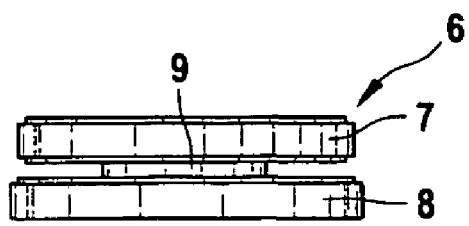
FIGS. 4a to 4g show a sequence of movements of the drive device.
Figure 4B:
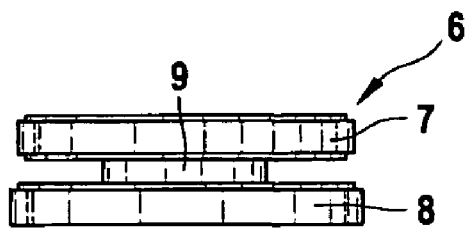
Figure 4C:
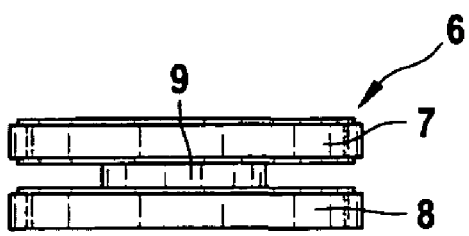
Figure 4D:
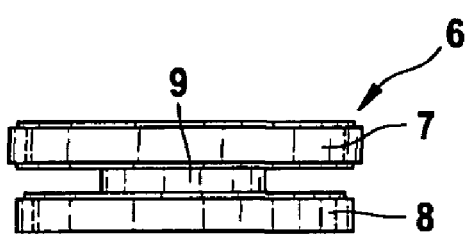
Figure 4E:
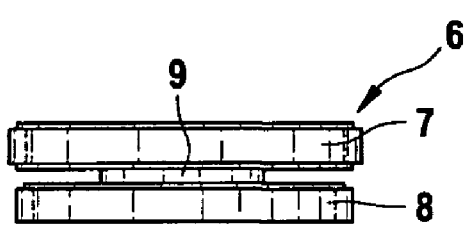
Figure 4F:
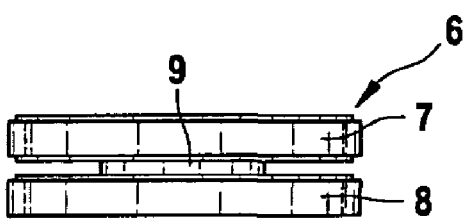
Figure 4G:
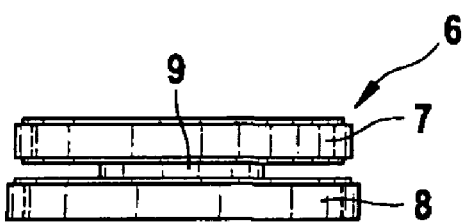

The sequence of movements illustrated in FIGS. 4a-4g show how the two segments 7, 8 and the connecting segment 9 interact to advance the piston (not shown) in the container (not shown). The sequence of movements is represented in 6 steps, wherein the step illustrated in FIG. 4g is identical to the first step illustrated in FIG. 4a, and is repeated after the sixth step (FIG. 4f).

Step 1 (FIG. 4a) represents the position of rest of the drive device 6. All three actuators, which are associated with the first segment 7, the connecting segment 9 and the second segment 8, are inactive. In the inactive case the first segment 7 is small, the connecting segment 9 is short and the second segment 8 is large. By activating the appropriate actuator the first segment 7 is large, the connecting the segment 9 is long and the second segment 8 is small. The condition (active or inactive) of the appropriate actuator in the different movement steps 1 to 6 (FIGS. 4a to 4f) can be seen in the following table:

|  | Movement Step | | | | | |
| --- | --- | --- | --- | --- | --- | --- |
|  | 1 (FIG. 4a) | 2 (FIG. 4b) | 3 (FIG. 4c) | 4 (FIG. 4d) | 5 (FIG. 4e) | 6 (FIG. 4f) |
| Actuator of the first segment 7 | I | I | A | A | A | A |
| Actuator of the connecting segment 9 | I | A | A | A | I | I |
| Actuator of the second segment 8 | I | I | I | A | A | I | where I means that the actuator is inactive and A means that the actuator is active.

When a segment 7, 8 is large it is clamped between the lateral walls of a container, and when it is small it is released from the lateral walls of the container. In step 1 (FIG. 4a) the second segment 8 is clamped and the first segment 7 is released. In step 2 (FIG. 4b) the connecting segment 9 is long and pushes the first segment 7 upwards. In step 3 (FIG. 4c) both segments 7, 8 are clamped. In step 4 (FIG. 4d) the first segment 7 is clamped and the second segment 8 is released. In step 5 (FIG. 4e) the connecting segment 9 is short and pulls the second segment 8 upwards. In step 6 (FIG. 4) both segments 7, 8 are clamped. The position of rest is then regained with step 1 (FIG. 4g).

In the embodiment shown in FIGS. 4a to 4g the drive device 6 for the piston of a container (ampoule) consists of the two segments 7, 8, which are connected to each other by an actuator as connecting element 9. The lower segment 8 contains an external clamping ring which normally clamps the segment 8 against the inner wall of the ampoule. This clamping is released by compressing the clamping ring with a further actuator. The upper segment 7 also contains an external, but normally stress-relieved clamping ring which can be clamped with an actuator against the inner wall of the ampoule. At the beginning of a movement (FIG. 4a—Step 1) the actuator of the lower segment 8 is relieved and the lower segment 8 is therefore fixed against the ampoule. The actuator of the upper segment 7 is also relieved and the upper segment 7 can therefore be moved against the ampoule. The actuator 9, which connects both segments together, is activated (FIG. 4b—Step 2). Because of this the upper segment 7 moves upwards and carries the piston 10 of the ampoule with it. If the movement is terminated the actuator on the clamping ring of the upper segment 7 is activated (FIG. 4c—Step 3) and the segment 7 is clamped against the wall of the ampoule. The actuator on the clamping ring of the lower segment 8 is then activated and the clamping is released (FIG. 4d—Step 4). The actuator 9 between both segments 7, 8 is deactivated (FIG. 4e—Step 5) and the lower segment 8 therefore moves upwards towards the upper segment 7. The actuator on the clamping ring of the lower segment 8 is deactivated, (FIG. 4f—Step 6) and the lower segment 8 is clamped again against the wall of the ampoule. The actuator on the clamping ring of the upper segment 7 is then deactivated (FIG. 4g—Step 1). This terminates a movement cycle and all the actuators are deactivated. Because of a multiplicity of such cycles the ampoule can be drained in a controlled manner.

In order to remove the drive device from the ampoule the actuator of the lower segment 8 is activated and the actuator of the upper segment 7 remains deactivated. As a result the clamping is fully released and the drive 6 can be pulled on connecting cables or a guard wire 12 from the ampoule.

The invention claimed is:

1. A drive device for a piston in a container containing a liquid product, the container having limiting lateral walls that extend in a longitudinal direction toward an outlet for the liquid product, the drive device comprising:
   a first segment having an actively variable shape, the first segment having a first shape in which the first segment is clamped between the lateral walls of the container and having a second shape in which the first segment is released from the lateral walls,
   a first paraffin actuator configured to actively vary the first segment between its first and second shapes,
   a second segment having an actively variable shape, the second segment having a first shape in which the second segment is clamped between the lateral walls of the container and having a second shape in which the second segment is released from the lateral walls, the first segment being positioned between the second segment and the outlet,
   a second paraffin actuator configured to actively vary the second segment between its first and second shapes, and
   a connecting segment connecting the first segment to the second segment, the connecting segment having an actively variable connecting length,
   wherein the container has a circular cross section,
   wherein the first segment comprises a first clamping ring that is clamped in its first shape to an inner wall of the container and is released from the inner wall in its second shape,
   wherein the second segment comprises a second clamping ring that is clamped in its first shape to the inner wall of the container and is released from the inner wall in its second shape,
   wherein the first clamping ring defines a first ring diameter that can be varied by activating the first paraffin actuator,
   wherein the second clamping ring defines a second ring diameter that can be varied by activating the second paraffin actuator,
   wherein the first clamping ring comprises a first open ring with two tongues projecting into the first open ring,
   and wherein the first paraffin actuator is positioned between the two tongues of the first open ring and has a thickness that is actively variable.

2. The drive device of claim 1 wherein the first paraffin actuator is actively variable between first and second thicknesses, the first paraffin actuator acting on the two tongues of the first open ring with its first thickness to control the first ring diameter of the first clamping ring to clamp the first clamping ring to the inner wall of the container,
   and wherein the first paraffin actuator has a second thickness that is less than its first thickness, the first paraffin actuator acting on the two tongues with its second thickness to control the first ring diameter of the first clamping ring to release the first clamping ring from the inner wall of the container.

3. The drive device of claim 2 wherein the first paraffin actuator assumes its first thickness when inactive and assumes its second thickness when activated.

4. A drive device for a piston in a container containing a liquid product, the container having limiting lateral walls that extend in a longitudinal direction toward an outlet for the liquid product, the drive device comprising:
   a first segment having an actively variable shape, the first segment having a first shape in which the first segment is clamped between the lateral walls of the container and having a second shape in which the first segment is released from the lateral walls,
   a first paraffin actuator configured to actively vary the first segment between its first and second shapes,
   a second segment having an actively variable shape, the second segment having a first shape in which the second segment is clamped between the lateral walls of the container and having a second shape in which the second segment is released from the lateral walls, the first segment being positioned between the second segment and the outlet,
   a second paraffin actuator configured to actively vary the second segment between its first and second shapes, and
   a connecting segment connecting the first segment to the second segment, the connecting segment having an actively variable connecting length, wherein the container has a circular cross section, wherein the first segment comprises a first clamping ring that is clamped in its first shape to an inner wall of the container and is released from the inner wall in its second shape, wherein the second segment comprises a second clamping ring that is clamped in its first shape to the inner wall of the container and is released from the inner wall in its second shape, wherein the first clamping ring defines a first ring diameter that can be varied by activating the first paraffin actuator, wherein the second clamping ring defines a second ring diameter that can be varied by activating the second paraffin actuator, and wherein the second segment comprises:

a baseplate, a second open ring with two tongues projecting into the second open ring, one of the two tongues of the second open ring being attached to the baseplate, and a thrust bearing attached to the baseplate adjacent to the other of the two tongues of the second open ring, wherein the second paraffin actuator is positioned between the thrust bearing and the other of the two tongues of the second open ring, the second paraffin actuator having a thickness that is actively variable.

5. The drive device of claim 4 wherein the second paraffin actuator is actively variable between first and second thicknesses, the second paraffin actuator acting on the thrust bearing and the other of the two tongues of the second open ring with its first thickness to control the second ring diameter of the second clamping ring to clamp the second clamping ring to the inner wall of the container, and wherein the second paraffin actuator has a second thickness that is greater than its first thickness, the second paraffin actuator acting on the thrust bearing and the other of the two tongues of the second open ring with its second thickness to control the second ring diameter of the second clamping ring to release the second clamping ring from the inner wall of the container.

6. The drive device of claim 5 wherein the second paraffin actuator assumes its first thickness when active and assumes its second thickness when inactive.

7. A drive device for a piston in a container containing a liquid product, the container having limiting lateral walls that extend in a longitudinal direction toward an outlet for the liquid product, the drive device comprising:

a first segment having an actively variable shape, the first segment having a first shape in which the first segment is clamped between the lateral walls of the container and having a second shape in which the first segment is released from the lateral walls, the first segment comprising a first clamping ring defining a first ring diameter that can be actively varied, the first clamping ring comprising a first open ring with two tongues projecting into the first open ring, a first actuator configured to actively vary the first segment between its first and second shapes, the first segment being in its first shape when the first actuator is inactive, the first ring diameter of the first clamping ring being varied by activating the first actuator, the first actuator comprising a first paraffin actuator positioned between the two tongues of the first open ring, the first paraffin actuator having a thickness that is actively variable, a second segment having an actively variable shape, the second segment having a first shape in which the second segment is clamped between the lateral walls of the container and having a second shape in which the second segment is released from the lateral walls, the second segment comprising a second clamping ring defining a second ring diameter that can be varied by activating the second actuator, the first segment being positioned between the second segment and the outlet, a second actuator configured to actively vary the second segment between its first and second shapes, the second actuator being in its second shape when the second actuator is inactive, and a connecting segment connecting the first segment to the second segment, the connecting segment having an actively variable connecting length.

8. The drive device of claim 7 wherein the first segment is rigidly connected to the piston.

9. The drive device of claim 7 wherein the first segment is integral with the piston.

10. The drive device of claim 7 wherein the first segment assumes its second shape when the first actuator is activated, and wherein the second segment assumes its first shape when the second actuator is activated.

11. The drive device of claim 7 wherein the connecting segment has a first connecting length and a second connecting length that is longer than the first connecting length.

12. The drive device of claim 11 wherein the connecting segment is a third actuator having a length, the third actuator configured to actively vary its length between the first and second connecting lengths.

13. The drive device of claim 11 further comprising a third actuator configured to actively vary the connecting length of the connecting segment between the first and second connecting lengths.

14. The drive device of claim 7 wherein the first paraffin actuator is actively variable between first and second thicknesses, the first paraffin actuator acting on the two tongues of the first clamping ring with its first thickness to control the first ring diameter of the first clamping ring to clamp the first clamping ring to the inner wall of the container, and wherein the first paraffin actuator has a second thickness that is less than its first thickness, the first paraffin actuator acting on the two tongues with its second thickness to control the first ring diameter of the first clamping ring to release the first clamping ring from the inner wall of the container.

15. The drive device of claim 14 wherein the first paraffin actuator assumes its first thickness when inactive and assumes its second thickness when activated.

16. The drive device of claim 7 wherein the second segment further comprises:

a baseplate, a second open ring with two tongues projecting into the second open ring, one of the two tongues of the second open ring being attached to the baseplate, and a thrust bearing attached to the baseplate adjacent to the other of the two tongues of the second open ring, wherein the second actuator comprises a second paraffin actuator positioned between the thrust bearing and the other of the two tongues of the second open ring, the second paraffin actuator having a thickness that is actively variable.

17. The drive device of claim 16 wherein the second paraffin actuator is actively variable between first and second thicknesses, the second paraffin actuator acting on the thrust bearing and the other of the two tongues of the second open ring with its first thickness to control the second ring diameter of the second clamping ring to clamp the second clamping ring to the inner wall of the container, and wherein the second paraffin actuator has a second thickness that is greater than its first thickness, the second paraffin actuator acting on the thrust bearing and the other of the two tongues of the second open ring with its second thickness to control the second ring diameter of the second clamping ring to release the second clamping ring from the inner wall of the container.

18. The drive device of claim 17 wherein the second paraffin actuator assumes its first thickness when active and assumes its second thickness when inactive.

* * * * *